(12) United States Patent
Hauri et al.

(10) Patent No.: US 8,534,848 B2
(45) Date of Patent: Sep. 17, 2013

(54) MARKER FOR A NAVIGATION SYSTEM

(76) Inventors: Bernhard Hauri, Staffelbach (CH);
Thomas Hauri, Staffelbach (CH)

( * ) Notice: Subject to any disclaimer, the term of this patent is extended or adjusted under 35 U.S.C. 154(b) by 136 days.

(21) Appl. No.: 13/121,647

(22) PCT Filed: May 5, 2009

(86) PCT No.: PCT/EP2009/055413
§ 371 (c)(1),
(2), (4) Date: Aug. 5, 2011

(87) PCT Pub. No.: WO2009/135838
PCT Pub. Date: Nov. 12, 2009

(65) Prior Publication Data
US 2011/0286098 A1 Nov. 24, 2011

(30) Foreign Application Priority Data
May 6, 2008 (DE) .......................... 10 2008 022 254

(51) Int. Cl.
*G02B 5/12* (2006.01)
(52) U.S. Cl.
USPC ......................................... 359/515; 359/543

(58) Field of Classification Search
USPC ................ 359/515, 543; 600/406, 407, 424, 600/427, 428
See application file for complete search history.

(56) References Cited

U.S. PATENT DOCUMENTS
2007/0183041 A1 * 8/2007 McCloy et al. ................ 359/515
2007/0225599 A1 9/2007 Solar et al.

FOREIGN PATENT DOCUMENTS
EP 1658819 A 5/2006
WO 03020146 A 3/2003

OTHER PUBLICATIONS
English translation of International Preliminary Examination Report for PCT/EP2009/055413, dated Nov. 17, 2010, 8 pages.

* cited by examiner

*Primary Examiner* — Euncha Cherry
(74) *Attorney, Agent, or Firm* — Michael Best & Friedrich LLP

(57) ABSTRACT

A marker for a navigation system for determining the spatial position (e.g., of a surgical instrument), said marker including a retroreflective ball (12). A retroreflective surface (13) of the ball (12) is protected by a dimensionally stable, translucent or transparent shell (14) in such a way that the reflected image remains essentially uninfluenced in terms of contour and the position of the centre of gravity.

19 Claims, 3 Drawing Sheets

MARKER FOR A NAVIGATION SYSTEM

CROSS REFERENCE TO RELATED APPLICATIONS

This application is a Section 371 national phase application of international patent application number PCT/EP2009/055413, the entire contents of which are hereby incorporated by reference herein.

BACKGROUND

The present invention relates to a marker for a navigation system.

Markers are used, for example in image-assisted surgical procedures (IGS=Image Guided Surgery), for ascertaining the position of surgical instruments or bodies connected to, for example, a plurality of markers in the form of a reference star, by means of optical detection of the light reflected by the markers, and, on the basis of the ascertained positional information, carrying out a surgical intervention.

Surgical navigation systems are accordingly used for measuring geometric variables (usually in a sterile context) in the course of surgical interventions on human beings and animals. A much used measurement technique is, as already mentioned, the positional measurement of optical markers using a light-optical camera system. Either these optical markers are self-illuminating (=active markers) or they reflect light produced by a flash-illumination camera system (=passive markers). On account of the particular conditions, especially in the sterile context of a surgical intervention, passive elements have advantages because they do not require a power supply of their own. In a process of sterile re-processing (washing in a washing machine, or sterilisation at 134° C. in steam), an energy supply and illuminating elements place very high demands on the resilience and construction of such components.

In the case of the passive markers, the light shining along the optical axis of the measuring objective, which light is usually produced by annular flash lamps arranged surrounding the camera objective, is reflected in the opposite direction (=retroreflection). Because the positional measurement of a surgical instrument or of the geometry of a body to be measured should be independent of the viewing angle, the use of spherical markers represents the simplest and most reliable solution from a measurement technique point of view. Irrespective of the viewing direction, a sphere always projects to a circle, whereas flat geometries, such as disc-shaped markers, produce distorted images or contours, for example contours similar to ellipses, which can be evaluated only with relatively great difficulty. Depending on the application, the diameter of the marker spheres preferably used is between 5 mm and 20 mm.

Retroreflection is achieved by means of a specially formed surface. Coatings having very fine prisms or coatings having very fine glass spheres embedded in the surface are known. Typical dimensions of those very fine glass spherules are between 20μ and 200μ. Given a suitable refractive index relative to the surrounding air and given suitable reflection properties of the embedding surface, which in the case of glass spherules represents a miniaturised hollow mirror, the incident light is retroreflected. Such surfaces are widely used in security technology and are often produced in foil form.

Because of the fineness of the glass spherules, a retroreflecting surface is rough at a micro scale. If such a retroreflecting surface is covered with a substance which is not transparent, for example dirt particles or blood, this region appears as a dark spot in the imaging by the camera. Because of the roughness at a micro scale, the removal of such soiling is laborious and also very often incomplete because dirt remains behind in the gaps between the glass spherules. If such a surface is wetted with a transparent medium, for example water, the surface loses its retroreflecting property because of the disrupted "air-glass spherule" beam path. In the image of the measuring camera, a retroreflecting surface wetted with water appears dark and cannot be used for measurement.

In respect of the formation of retroreflecting marker spheres, reference is made additionally to FR 2 706 045 A1. As far as the use of such marker spheres in surgery is concerned, reference is made to WO 2007/090288 A1.

SUMMARY

In order to avoid the afore-mentioned disadvantages caused by soiling or wetting of retroreflecting surfaces, the latter have been so covered with a foil that the foil maintains a small spacing from the retroreflecting surface. Dirt or the like can be easily wiped off the smooth foil surface. Wetting with water disrupts the beam path only insubstantially. The beam-optical "air-glass spherule" transition is ensured by the small air gap between the protective foil and the retroreflecting surface. As spacers between the protective foil and the retroreflecting surface, a honeycomb pattern is used. Such arrangements can still be produced relatively well in the case of flat surfaces. For spherical, especially ball-shaped, surfaces, the known protective foils are unsuitable. Undefined distortions are produced. Consequently, the accuracy of the positional determination is limited, especially when marker recognition algorithms based on the detection of the centre of mass are used (see also EP 1 774 922 A1 in this regard).

For that reason there continue to be used in practice either unprotected marker spheres or foil-protected flat markers. As mentioned, flat marker elements protected against dirt have the advantage that they can be easily cleaned but the disadvantage that the imaging recorded by a measuring camera is distorted. Unprotected marker spheres have the advantage of imaging that is ideal from a measurement technique point of view but the disadvantage of being readily soiled and of retroreflection being disrupted by wetting with water or like transparent liquids.

The present invention is accordingly based on the problem of making available a marker which has the advantages of the two afore-mentioned systems whilst simultaneously avoiding their disadvantages.

One aspect of the present invention is, accordingly, the covering-over of a spherical retroreflecting surface, especially a retroreflecting sphere, with a light-permeable or transparent (i.e., translucent) shell, more specifically in such a manner that the reflecting image, in respect of contour and barycentre location, is substantially uninfluenced by the shell. As a result of the shell according to the invention, the imaging, ideal from a measurement technique point of view, of a light emitted by a light source and reflected by the reflecting surface, in an associated measuring camera, should accordingly not be disadvantageously influenced. Circular imaging of the retroreflecting surface by the camera is ideal. The shell used in accordance with the invention should be dimensionally stable so that spacer elements between the retroreflecting surface and the shell can be avoided. As a result, undisrupted imaging, in the camera, of the light reflected by the retroreflecting surface can be ensured. The image is not altered by the dimensionally stable, translucent shell in respect of contour and barycentre location.

Because customary retroreflection surfaces work only in the context of air or gaseous media having a refractive index close to "1", it is necessary for the shell protecting the retroreflecting surface to be arranged at a small spacing from the retroreflecting surface. Preferably, the shell is spaced away from the retroreflecting surface in the range between 0.1 mm to 0.5 mm, especially in the range between about 0.3 mm to 0.4 mm.

In a first arrangement, the dimensionally stable, translucent shell consists of two shell halves which can be adhesively bonded or welded to one another and which concentrically surround the retroreflecting surface, especially the sphere. In this arrangement, distortion of the reflected image is ruled out over the entire retroreflecting surface, especially the sphere surface.

The thickness of the shell protecting the retroreflecting surface is about 0.7 mm to 1.2 mm, especially about 1.0 mm. It is made preferably from highly transparent plastics material. Glass is also feasible as a material for the shell even if manufacture from glass is more costly.

The sphere shell matched to the retroreflection sphere best meets, as mentioned, in terms of the imaging geometry, the conditions mentioned at the outset for undistorted imaging of the incident light reflected by the retroreflection surface. In view of the fact that the shell is and also has to be made from two parts, connection problems do of course arise, which are, however, surmountable using current-day adhesive bonding and welding technology. The connection must of course be so formed that the optical transparency remains substantially undisrupted.

Another arrangement is characterised in that the shell protecting the retroreflecting surface is of one-piece construction. Consequently, the shell includes a hood placed over the retroreflecting surface, especially the sphere, having a spherical hood portion and a cylindrical portion adjacent thereto. This arrangement is relatively simple in terms of manufacture. The protective hood can be manufactured as an injection-moulded part. Onto the free end of the cylindrical portion there is preferably formed a flange by means of which fixing to a supporting plate which need no longer be transparent or translucent is carried out. This supporting plate can be connected to, especially mounted on, a supporting rod or supporting adaptor of the navigation system.

In order to obtain, even in the region of the cylindrical portion, imaging that is free from distortion, especially circular imaging of the retroreflecting surface, that portion has optical correction regions, for example in the form of an outer peripheral surface that extends conically outwards in the axial direction starting from or below the transition between the cylindrical portion and the spherical hood portion. In this context it should be borne in mind that, in practice, retroreflection spheres are used up to a viewing angle of about 70° relative to the central axis defined by the supporting rod. As a result of the mentioned measures in the cylindrical portion, circular imaging of the retroreflecting surface, especially the sphere surface, can still be obtained by the camera even in the region of a viewing angle of close to 70°.

It is known that an image of a retroreflecting sphere is not actually an image of an article in the usual sense but rather represents an intensity distribution of the retroreflected light amounts over the sphere surface as seen by the camera. Consequently, in the case of the latter arrangement with lateral oblique viewing, given the correction measures, for example on the outer wall of the cylindrical portion, the lower reflection loss due to a less slanting light passage through the cylindrical portion compared to the increasingly more slanting light passage through the spherical hood portion of the transparent or translucent protective hood is to be taken into account.

Hereinbelow there are explained in greater detail two examples of embodiments of a marker constructed in accordance with the invention with reference to the accompanying drawings.

DETAILED DESCRIPTION

Figure 1:
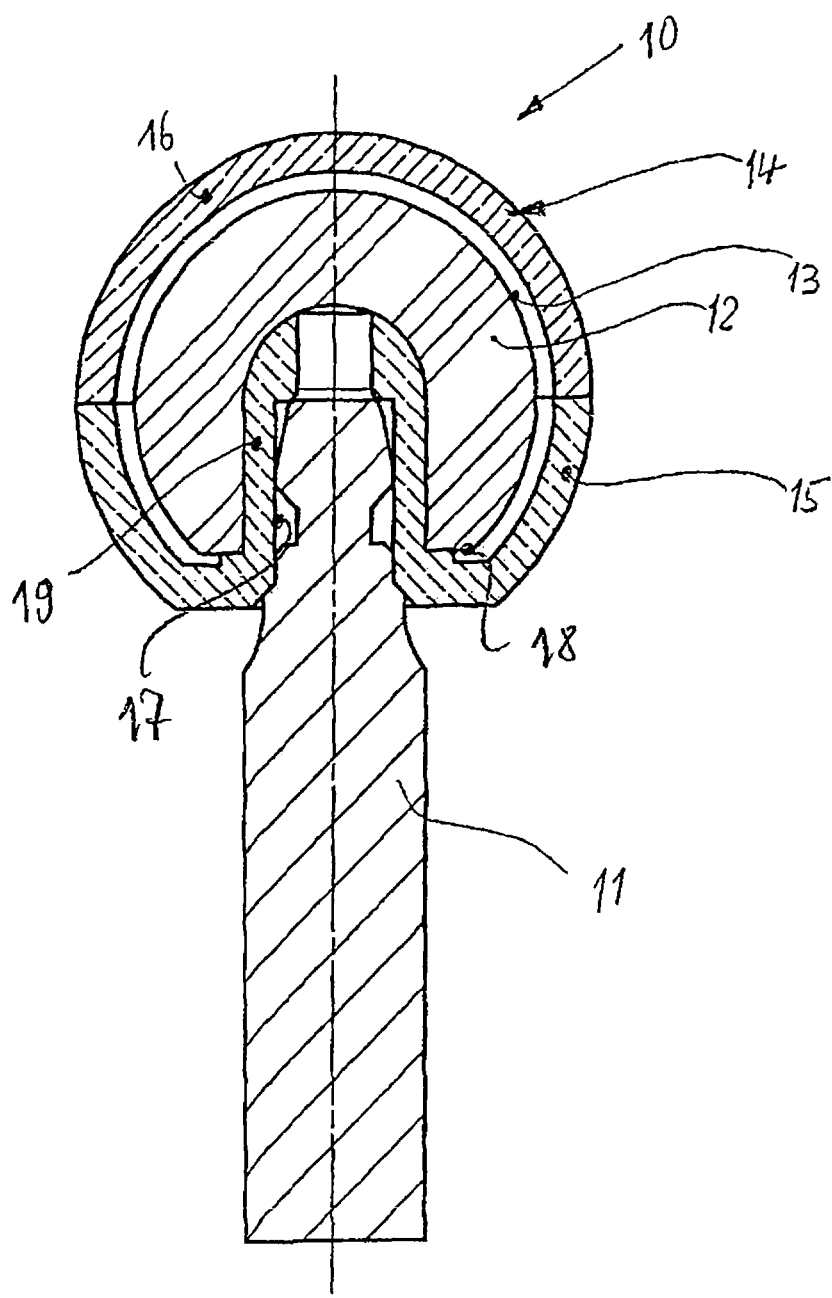
FIG. 1 shows, in longitudinal section, a first arrangement of a marker constructed in accordance with the invention.

FIG. 1 shows, in longitudinal section and to an enlarged scale, a marker 10 for a navigation system for determining the position in space, of, for example, a surgical instrument. This marker 10 comprises a sphere 12 having a retroreflecting surface 13, which in known manner includes very fine glass spherules having a diameter from 20µ to a maximum of about 200µ. The retroreflecting surface 13 is protected by a dimensionally stable, light-permeable or transparent (i.e., translucent) shell 14, preferably made of transparent plastics material, more specifically in such a manner that the reflected image remains substantially uninfluenced in respect of contour and barycentre location. As mentioned hereinbefore, imaging of the retroreflecting sphere surface by a camera associated with the system ideally is circular. As a result of the fact that the shell 14 concentrically surrounds the retroreflecting sphere surface 13 at a small spacing and also that the wall thickness of the shell 14 is constant in the region of the retroreflecting surface, no distortions are produced by the shell 14 on imaging of the retroreflecting sphere surface 13 by a camera associated with the system. As a result, it is possible, especially, to ensure imaging of the retroreflecting sphere surface that ideally is circular.

The translucent shell 14, the wall thickness of which is between 0.7 mm to 1.2 mm, especially about 1.0 mm, is, as already mentioned, spaced away from the retroreflecting surface 13 very slightly, the spacing being between about 0.1 mm to 0.5 mm, especially about 0.3 mm to 0.4 mm. The gap between the retroreflecting surface 13 and the shell 14 is filled with air or nitrogen, that is to say with a gas whose refractive index is about "1". The gas is dehumidified to the maximum so that the risk of any moisture being precipitated or of corrosion is ruled out. The sphere 12 of the retroreflecting surface 13 is also encapsulated by the shell 14 in air-tight manner relative to the external environment so that no moisture can penetrate into the gap between the sphere 12 and the shell 14 either.

In the shown arrangement according to FIG. 1, the translucent shell 14 consists of two shell halves 15, 16, which can be adhesively bonded or welded, especially ultrasonically welded, to one another and which concentrically surround the retroreflecting surface 13 or sphere 12. The bottom shell half 15 has a blind-hole-like recess 17, into which there can be inserted a supporting rod or mounting pin 11 associated with a navigation system (not shown in further detail).

The sphere 12 having the retroreflecting surface 13 can be placed on that wall of the bottom shell half 15 which delimits the blind hole 17. The sphere 12 is then not a complete sphere but rather a sphere truncated on one side. With the truncated region 18 leading, the sphere 12 is placed on the wall 19 of the blind hole. In this case the fit between the wall 19 of the blind hole and the sphere 12 is such that air-tight closure between those two parts is ensured. As a result, moisture cannot penetrate into the gap between the sphere 12 or its retroreflecting surface 13 and the shell 14 from the outside by way of the blind hole 17 either.

Figure 2:
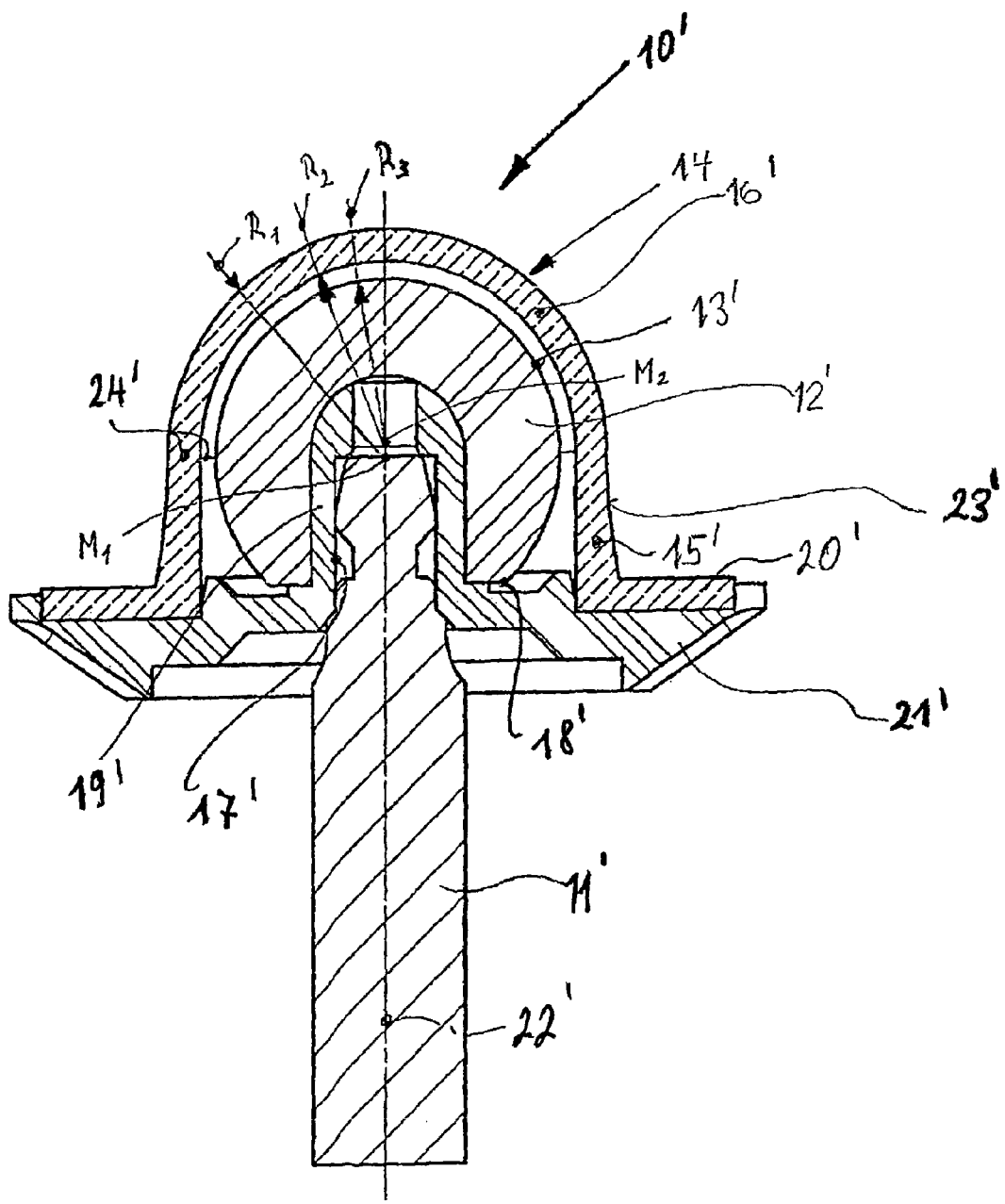
FIG. 2 shows, in longitudinal section, a second arrangement of a marker constructed in accordance with the invention.

The arrangement according to FIG. 2 differs from that according to FIG. 1 in that the shell 14 protecting the retroreflecting surface 13' of the marker sphere 12' is in the form of a hood, placed over the sphere 12', having a spherical hood portion 16' and a cylindrical portion 15' adjacent thereto. The shell 14 according to FIG. 2 is accordingly of one-piece construction.

Onto the free bottom end of the cylindrical portion 15 there is formed a flange 20', by means of which fixing to a supporting plate 21' is carried out. Insofar as the supporting plate 21', like the hood 14, is made from plastics material, the connection is made preferably by adhesive bonding or ultrasonic welding. In the supporting plate 21' there is centrally formed a blind hole 17' for receiving the mounting pin 11'. Onto the wall 19' delimiting the blind hole 17' there is placed the marker sphere 12' in the manner described with reference to FIG. 1, more specifically also with the truncated portion 18' leading again. The connection between the hood 14 and the supporting plate 21' is air-tight so that, in the case of this arrangement too, the marker sphere 12 having the retroreflecting surface 13' is encapsulated relative to the external environment. In this case too, no moisture can penetrate from the outside into the gap between the retroreflecting surface 13' and the hood 14.

The cylindrical portion 15' preferably includes optical correction regions for ensuring circular imaging of the retroreflecting surface 13' even close to the maximum viewing angle relative to the central axis 22' of the shown arrangement. The maximum viewing angle is about 70° to 75°. In this region too, it should also be ensured that imaging of the retroreflecting sphere surface by the associated camera of the system is circular.

For that purpose, in concrete terms, the outer peripheral surface 23' of the cylindrical portion 15' extends conically outwards in the axial direction starting from or below the transition 24' between the cylindrical portion 15' and the spherical hood portion 16'. The angle between the central axis 22' and the peripheral surface extending conically outwards is about 5° to 12°, especially about 8° to 10°. Ultimately that angle depends on the maximum viewing angle range, the material and the dimensions of the sphere and protective hood.

In the case of the last-mentioned arrangement it is also of interest that the centre-point $M_2$ of the inner radius $R_2$ of the spherical hood portion 16' is displaced inwards, that is to say into the spherical hood portion 16', relative to the centre-point $M_1$ of the outer radius $R_1$ of that portion, as is shown in FIG. 2. The centre-point $M_2$ is also the centre-point of the radius $R_3$ of the retroreflecting surface 13'.

The spacing between the centre-points $M_1$ and $M_2$ located on the central axis 22' is about 0.08 mm to about 0.12 mm, especially about 0.1 mm, insofar as the radii $R_1$, $R_2$ and $R_3$ are dimensioned approximately as follows:

$R_1$=6.4 mm to 70 mm
$R_2$=5.4 mm to 60 mm
$R_3$=5.2 mm to 5.7 mm.

The spherical hood portion 16' of the arrangement according to FIG. 2 can also be of preferably aspherical construction in order to ensure circular imaging of the retroreflecting surface 13'. This is a question of fine tuning in such a way that the requirement for circular imaging of the retroreflecting sphere surface by a camera associated with the system is met.

Regarding the material of the shell 14 it should be further mentioned that the refractive index of the material should be about 1.5.

Regarding the above-mentioned offset between the centrepoints $M_1$ and $M_2$ it should also be further mentioned that it produces a predetermined refraction correction resulting from the specific arrangement according to FIG. 2, that is to say from the combination of a hemispherical hood portion 16' and a cylindrical portion 15'.

Figure 3:
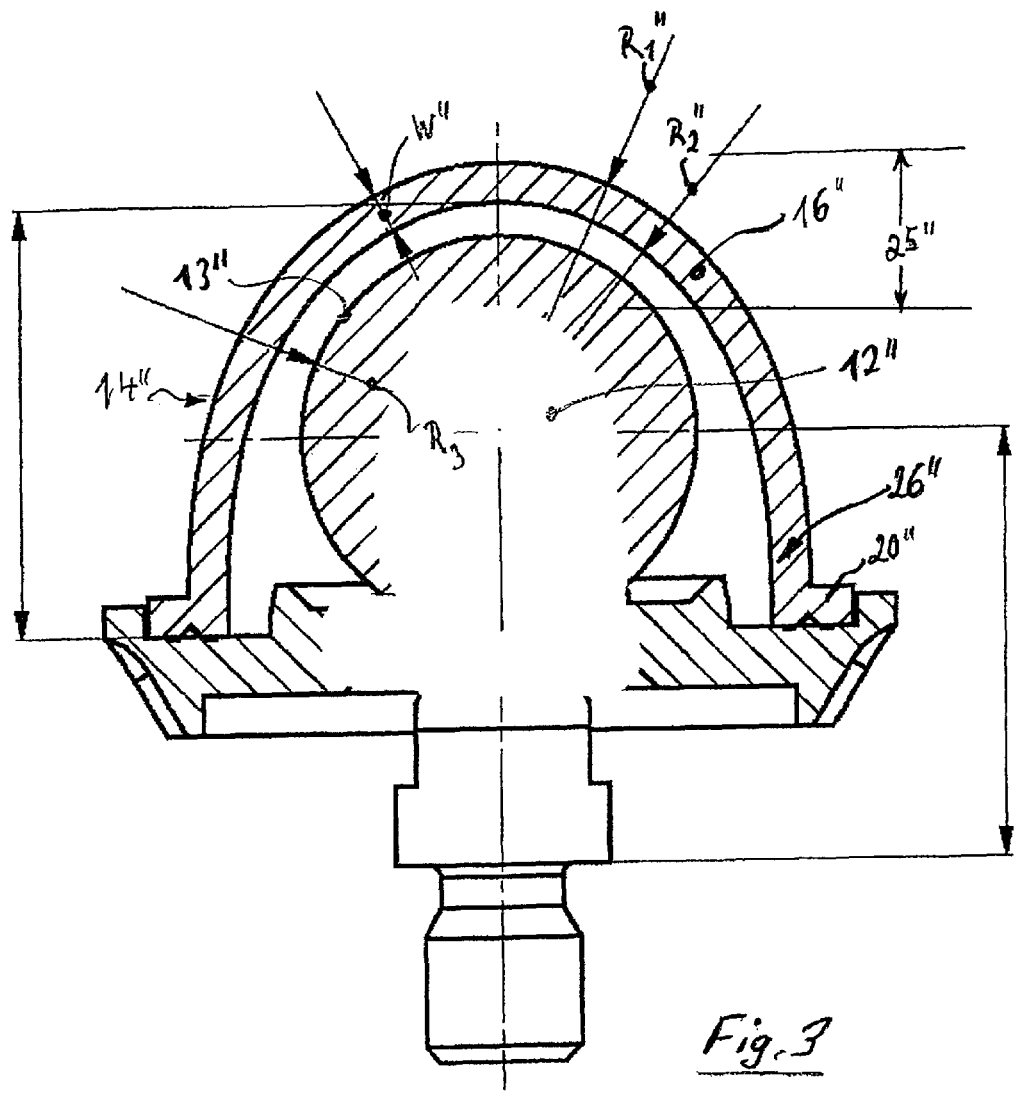
FIG. 3 shows, in longitudinal section, a third arrangement of a marker according to the invention.

The arrangement according to FIG. 3 is characterised in that the afore-mentioned refraction correction is obtained by means of an aspherical hood 16", which has the same wall thickness W" throughout. In the top third 25", the hood 16" is spherical. Subsequently the hood continuously widens out aspherically in the direction of the flange 20" with a corresponding increase in the outer and inner hood radii $R_{1''}$ and $R_{2''}$. Close to the flange 20", the hood 16" asymptotically approximates to a vertical (vertically extending asphere 26"). Reference numeral 12" denotes the sphere defining the retroreflecting surface.

The invention claimed is:

1. A marker (10, 10') for a navigation system configured to determine the position in space of a surgical instrument, the marker comprising:
    a spherical retroreflecting surface (13, 13') in the form of a retroreflecting sphere (12, 12'); and
    a dimensionally stable translucent shell (14) that protects the retroreflecting surface in such a way that a reflecting image is substantially uninfluenced by the shell in respect of contour and barycentre location,
    wherein the shell (14") includes a hood (16") placed over the retroreflecting surface (13"), wherein the hood (16") includes a spherical hood portion (25") and an aspherical hood portion adjacent thereto, and wherein the hood (16") terminates in a vertically extending asphere (26").

2. The marker of claim 1, wherein the shell (14) is transparent.

3. The marker of claim 1, wherein the shell (14) is spaced away from the spherical retroreflecting surface (13, 13') 0.1 mm to 0.5 mm.

4. The marker of claim 1, wherein the shell (14) is spaced away from the spherical retroreflecting surface (13, 13') 0.3 mm to 0.4 mm.

5. The marker of claim 1, wherein the shell (14) includes a first shell halve (15) and a second shell halve (16) configured to be at least one of adhesively bonded and welded together, and wherein the first and second shell halves concentrically surround the retroreflecting sphere (12).

6. The marker of claim 5, wherein the first shell halve (15) is a top shell halve and the second shell halve (16) is a bottom shell halve, wherein the bottom shell halve includes a blind-hole-like recess (17) configured to receive one of a supporting rod and a mounting pin (11), and wherein the blind-hole-like recess includes a boundary wall (19) on which the retroreflecting sphere (12) is placed.

7. The marker of claim 1, further comprising a gap between the retroflecting sphere (12, 12') and the shell (14), wherein the gap is filed with a gas having an optical refractive index of approximately 1.

8. The marker of claim 7, wherein the gas includes an inert gas.

9. The marker of claim 8, wherein the gas includes at least one of air and nitrogen.

10. The marker of claim 1, wherein the retroreflective sphere (12, 12') is encapsulated by the shell (14) in an air-tight manner relative to an environment.

11. The marker of claim 1, wherein the shell encloses the spherical retroreflecting surface.

12. A marker (10, 10') for a navigation system configured to determine the position in space of a surgical instrument, the marker comprising:
   a spherical retroreflecting surface (13, 13') in the form of a retroreflecting sphere (12, 12') and having a convex retroreflecting surface; and
   a dimensionally stable translucent shell (14) that protects the retroreflecting surface in such a way that a reflecting image is substantially uninfluenced by the shell in respect of contour and barycentre location.

13. The marker of claim 12, wherein the shell encloses the spherical retroreflecting surface.

14. The marker of claim 12, wherein the shell (14) includes a hood placed over the spherical retroreflecting surface (13'), and wherein the hood includes a spherical hood portion (16') and a cylindrical portion (15') adjacent thereto.

15. The marker of claim 14, wherein the cylindrical portion (15') includes optical correction regions at an outer peripheral surface (23') that extends conically outwards in an axial direction starting at one of from and below a transition (24') between the cylindrical portion (15') and the spherical hood portion (16'), and wherein the cylindrical portion (15') ensures circular imaging of the spherical retroreflecting surface (13') close to a minimum viewing angle.

16. The marker of claim 14, wherein a centre-point ($M_2$) of an inner radius ($R_2$) of a portion of the spherical hood portion (16') is displaced into the spherical hood portion (16') relative to the centre-point ($M_1$) of an outer radius ($R_1$) of the portion of the spherical hood portion (16').

17. The marker of claim 14, wherein the cylindrical portion (15') of the hood (14) includes a free end, wherein the shell (14) further includes a flange (20') adjacent the free end; a support plate (21') fixed to the flange (20'); and one of a supporting rod and mounting pin (11) connected to the support plate (21').

18. The marker of claim 14, wherein the spherical hood portion (16') is of aspherical construction for ensuring circular imaging of the spherical retroflecting surface.

19. The marker of claim 12, wherein the shell (14") includes a hood (16") placed over the retroreflecting surface (13"), wherein the hood (16") includes a spherical hood portion (25") and an aspherical hood portion adjacent thereto, and wherein the hood (16") terminates in a vertically extending asphere (26").

* * * * *

UNITED STATES PATENT AND TRADEMARK OFFICE
CERTIFICATE OF CORRECTION

PATENT NO. : 8,534,848 B2
APPLICATION NO. : 13/121647
DATED : September 17, 2013
INVENTOR(S) : Hauri et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 408 days.

Signed and Sealed this
Fifteenth Day of September, 2015

Michelle K. Lee
*Director of the United States Patent and Trademark Office*